United States Patent [19]
Chang

[11] Patent Number: 5,630,919
[45] Date of Patent: May 20, 1997

[54] ELECTRODE FOR CONDUCTIVITY CELLS COMPRISING HIGH SURFACE AREA METAL FOIL

[76] Inventor: On K. Chang, 1031 Belvedere La., San Jose, Calif. 95129

[21] Appl. No.: 400,123

[22] Filed: Mar. 6, 1995

Related U.S. Application Data

[63] Continuation of Ser. No. 49,062, Aug. 6, 1993, abandoned.
[51] Int. Cl.$^6$ .................. G01N 27/403; G01N 27/406; G01N 27/417
[52] U.S. Cl. ............................... 204/400; 204/421
[58] Field of Search ....................... 204/421, 400

[56] References Cited

U.S. PATENT DOCUMENTS

| | | | |
|---|---|---|---|
| 3,924,175 | 12/1975 | Wilson | 204/400 |
| 4,882,029 | 11/1989 | Eickman | 204/400 |

*Primary Examiner*—Prince Willis, Jr.
*Assistant Examiner*—Carol Chaney
*Attorney, Agent, or Firm*—Charles Jew

[57] ABSTRACT

An electrode for measuring the conductivity of liquid and solid electrolytes comprises an electrically conductive support having an effective amount of a high surface area metal foil thereon.

14 Claims, 1 Drawing Sheet

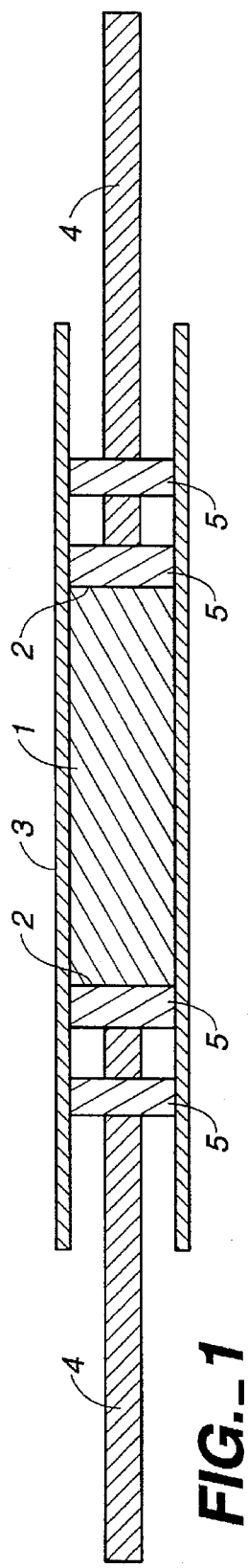
FIG._1
FIG._2

5,630,919

ELECTRODE FOR CONDUCTIVITY CELLS COMPRISING HIGH SURFACE AREA METAL FOIL

This application is a continuation of application Ser. No. 08/049,062, filed Aug. 6, 1993, now abandoned.

FIELD OF THE INVENTION

The present invention relates to an electrode for use in conductivity cells or probes. In particular, the electrode according to the present invention is capable of providing measurements at a decreased cost when compared to conventional electrodes.

BACKGROUND OF THE INVENTION

Conductivity cells and probes are a well recognized means for measuring the conductivity of electrolytes. Electrolytic conductance is the transport of electric charge under electric potential differences by particles of atomic or larger size. This phenomenon is distinguished from electronic or metallic conductance which is due to the movement of electrons. Electrolytic conductors may be solids, liquids or gases. Conductance is usually measured as the specific conductance, κ, which is the reciprocal of the resistance of a cube of material, 1 cm in each direction, placed between electrodes 1 $cm^2$, on opposite sides of the cube. Conductances of solutions and solids are usually measured by the Kohlrausch method in which a Wheatstone bridge is employed. The conductance cell containing the electrolytic conductor between electrodes is placed is one arm of the bridge. By using an alternating current between the electrodes of the cell, the electrochemical reactions are reversed on the half cycle. When a small alternating current is used for input signal to the electrodes, practically all the electric charge passed during each half cycle is stored in electric double layer which acts as a capacitor. The electrodes are usually made of platinum and are platinized, that is, coated with finely divided metallic platinum. The surface area of the electrode, and hence the electrode capacitance is thereby greatly increased. The coating of the electrodes is achieved by electrolysis of a 3% solution of chloroplatinic acid containing lead acetate. In some cases platinized electrodes cannot be used because the platinum catalyzes the decomposition of the electrolyte.

Recently, an improved conductivity cell for use with solid electrolytes has been produced. This cell, which was developed by Ib Olsen of Valence Technology, Inc., Denmark, is known as a syringe-type electrolyte-conductivity cell and is illustrated in FIG. 1. This cell is disclosed in U.S. patent application No. Ser. 08/042,315, and entitled, "ELECTRO-CHEMICAL TEST CELL FOR TRANSPORT AND CONDUCTIVITY MEASUREMENTS" which is incorporated herein by reference in its entirety.

Such a cell comprises a plastic barrel, 3, for example, adapted from a plastic syringe by cutting off the tip of the barrel, and a pair of stainless steel rods, 4, each having at least one O-ring 5, located thereon, to contain the electrolyte, 1, and maintain contact with the electrode surface, 2.

In using such a cell, a sample of unpolymerized electrolyte (liquid) can be placed into the syringe barrel and sealed between the two electrodes. The conductivity of the liquid sample can then be measured. This sample can then be cured in situ by employing ultraviolet radiation. The curing process converts the liquid electrolyte to a solid electrolyte which is suitable for use as an electrolyte in a solid battery.

Because of the difficulty of cleaning the electrodes of the conductivity cell it would be advantageous if the cell were disposable.

In any case, the electrodes which are employed in conductivity cells (as well as conductivity probes) need a high surface area in order to provide measurements. Furthermore, the electrodes must also be inert to both the liquid and solid electrolytes, to be tested. Traditional material for use in such electrodes is a high surface area form of platinum, known as platinum black which is produced by a plating process.

While electrodes made from such materials provide the desired degree of accuracy, they are also very expensive. Accordingly, the need still exists for an electrode which is capable of providing accurate results while being more cost effective.

SUMMARY OF THE INVENTION

In accordance with the foregoing objectives, the present invention relates to an electrode for use in measuring the conductivity of both liquid and solid electrolytes which comprises an electrically conducting electrode support connected to an active electrode surface, wherein the active electrode surface is covered with a nickel or copper foil. The surface of the metal foil is itself made up of finely divided metal particles having an average diameter of less than four microns.

In another aspect, the present invention relates to a conductivity cell or probe which includes this electrode.

In yet another aspect, the present invention relates to a method for measuring the conductivity of a liquid or solid which employs this electrode.

BRIEF DESCRIPTION OF THE DRAWINGS

FIG. 1 illustrates a syringe-type electrolyte conductivity cell;

FIG. 2 illustrates the surface of high surface area nickel foil.

DETAILED DESCRIPTION OF THE PREFERRED EMBODIMENTS

The electrodes of the present invention can be employed in any of those conductivity cells and probes recognized in the art such as a simple conductivity cell, the syringe-type conductivity cell of FIG. 1, and conductivity probes.

This electrode includes an active electrode surface defined by the presence of a high surface area nickel or copper foil. A high surface area nickel foil or a high surface area copper foil are found to be accurate conductance measuring tools for both liquid and solid electrolytes. Solid electrolytes for use in solid state secondary batteries are described in U.S. Pat. No. 4,925,751, the disclosure of which is incorporated herein by reference in its entirety. A high surface area nickel foil is most preferred for use in the present invention.

Accordingly, an electrode for use in measuring conductivity in accordance with this invention includes an electrically conductive electrode support. The electrode support is connected to an active electrode surface. The active electrode surface is covered with a nickel or copper foil having a high surface area.

The amount of foil which is employed in the electrode is that effective to cover the active surface of the electrode. This provides a cost-effective and useful measurement of conductivity upon use of the electrode. The "active surface" of an electrode in a conductivity cell is generally that portion of the surface of the electrode which is in electrolytic contact with the electrolyte.

By "high surface area" it is meant that the surface area is sufficient to provide for conductivity measurements. Typically, the foil includes a surface area which is at least about 3 times, preferably at least 6 times, its geometric area, with about 9 times its geometric area being more preferred.

A nickel or copper foil surface of finely divided metal particles having an average diameter less than about 4 microns is preferred. Such a metal foil surface may be prepared by electroplating in a solution containing a salt of the metal. As is well known to the art, the composition of the electrolyte in the electroplating, both influences the structure and surface finish of the metal coating. Numerous formulas, also known to the art, involving metallic complexes and organic additives have been developed for this purpose.

High surface area metal foils are known in the art. For example, high surface area nickel foil is commercially available from a variety of sources such as Fukuda Metal Foil, and Powder Co., Ltd., Kyoto, Japan. Such commercially available foils have a surface area of about 9 times their geometric area. See, for example, the high surface area nickel foil shown in FIG. 2.

The metal foil can be attached to a electrical conductive support by any means recognized in the art so as to form the electrode. For example, the foil can be welded onto the support. In that embodiment where an electrode rod is employed, e.g., in a syringe-type conductivity cell, the foil can be spot welded onto the ends of the rod.

Alternatively, the foil can be adhesively attached by any means, which is not soluble in the liquid in which it is being employed.

The electrical conductive supports which can be employed include those which are recognized in the art and are dependent upon the particular conductivity cell. For example, in a syringe-type conductivity cell a rod-shaped electrode is employed. In such an arrangement, suitable materials for such electrodes include stainless steel, Ni, Cu and brass with stainless steel being preferred.

In another embodiment of the invention, the electrode can be employed in those conductivity probes which are well recognized within the art. In particular, it can be employed in each of the major types of probes, e.g., the dipping-type probe, or the cup-type probe. Moreover, they can be employed in either the art recognized 2-electrode or 4-electrode cell design.

The electrodes according to the present invention provide conductivity measurements at a greatly reduced cost when compared to conventional electrodes employing platinum black.

In fact, due to the relatively low cost of certain metal foils such as Ni and Cu, with the appropriate selection of low-cost plastic and metal materials for use in the rest of the cell, the cell can be disposable.

By making measurements at several frequencies and extrapolating to infinite frequency, the effect of electrode reactions can be eliminated in the measurement of conductance. To determine the conductance C, that is, the reciprocal of resistance of the cell, the resistance of the bridge is adjusted until a balance is achieved. When the bridge is in balance, no current flows, and the conductance is given by the relationship of the bridge resistances. From C the specific conductance is obtained from the equation $\kappa=KC$, in which K is the cell constant. The cell constant can be computed from the dimensions of the cell, or determined by using a solution whose $\kappa$ value is accurately known from measurements in such cells. A solution of potassium chloride of known specific conductance $\kappa_0$ is placed in the cell and its resistance $R_0$ is measured; then the cell constant K is equal to $\kappa_0 R_0$. If the resistance of any other electrolyte in the cell is known, then its specific conductance $\kappa$ is K/R.

EXAMPLE

A syringe conducting cell of 0.470 cm inside diameter was assembled with a stainless steel electrode having O-rings. The cell was filled with KCl solution of 0.012856 $OHM^{-1}$ $cm^{-1}$ specific conductance. The resistance of the electrolyte was measured using a GENRAD "DIGIBRIDGE" and found to be $R_0=2.10\times10^3$ OHM. The cell constant from this measured resistance is $K=\kappa_0 R_0=0.012856$ $OHM^{-1}$ $cm^{-1}\times2.10\times10^3$ OHM. From this calculation K was found to be 27.0 $cm^{-1}$. The correct cell constant was calculated from the cell geometry as K=22.3 $cm^{-1}$ (from a cell length of 1.52 cm). This rather poor agreement indicates the need for modification of electrodes. The electrodes are modified by spot-welding a high surface area nickel foil to the electrode surface. The test was repeated and a resistance of $R_0=1.83\times10^3$ OHM was found. This a cell constant of 23.5 $cm^{-1}$, in good agreement with the cell constant calculated from cell geometry of 23.1 $cm^{-1}$ (cell length 1.58 cm).

While the invention has been described in terms of various preferred embodiments, the artisan will appreciate the various modifications, substitutions, and omissions, and changes that may be made without departing from the spirit thereof.

I claim:

1. A method for measuring the conductivity of an electrolyte comprising:
    (a) providing a conductivity cell that comprises (1) a generally longitudinal chamber having substantially the same thickness throughout its length; and (2) a pair of electrodes, each electrode comprising:
        (i) a rod-shaped support having an active electrode surface on at least a portion of one end of the support, said active electrode surface being a high surface area nickel or copper foil; and
        (ii) means for holding the electrode in place in the chamber,
    wherein the active electrode surface and holding means of one electrode are in one end of the chamber and the active electrode surface and holding means of the other electrode are in the other end of the chamber, and further wherein in the holding means positions the active electrode surface so as to define a volume in the chamber for holding the electrolyte and such that each active electrolyte surface is in contact with the electrolyte,
    (b) introducing a sample of unpolymerized liquid electrolyte into the conductivity cell and curing the sample with radiation to form a solid electrolyte; and
    (c) measuring the resistance of the solid electrolyte.

2. The method according to claim 1 wherein the high surface area foil includes a surface area which is not less than about 9 times its geometric area.

3. The method according to claim 2 wherein the foil is nickel foil.

4. The method according to claim 2 wherein the foil is copper foil.

5. The method according to claim 1 wherein the foil is nickel foil.

6. The method according to claim 1 wherein the foil is copper foil.

7. The method according to claim 1 wherein the foil comprises finely divided metal particles having an average diameter of less than 4 microns.

8. The method according to claim 1 wherein the foil comprises finely divided metal particles having an average diameter of less than 4 microns.

9. A method for measuring the conductivity of an electrolyte comprising:

(a) providing a conductivity cell that comprises (1) a generally longitudinal chamber having substantially the same thickness throughout its length; and (2) a pair of electrodes, each electrode comprising:

(i) a rod-shaped support having an active electrode surface on at least a portion of one end of the support, said active electrode surface being a high surface area nickel or copper foil; and (ii) means for holding the electrode in place in the chamber, wherein the active electrode surface and holding means of one electrode are in one end of the chamber and the active electrode surface and holding means of the other electrode are in the other end of the chamber, and further wherein in the holding means positions the active electrode surface so as to define a volume in the chamber for holding the electrolyte and such that each active electrolyte surface is in contact with the electrolyte, (b) introducing a sample of unpolymerized liquid electrolyte into the conductivity cell; and (c) measuring the resistance of the unpolymerized liquid electrolyte.

10. The method according to claim 9 wherein the high surface area foil includes a surface area which is not less than about 9 times its geometric area.

11. The method according to claim 10 wherein the foil is nickel foil.

12. The method according to claim 10 wherein the foil is copper foil.

13. The method according to claim 9 wherein the foil is nickel foil.

14. The method according to claim 9 wherein the foil is copper foil.

* * * * *